(12) United States Patent
Hall et al.

(10) Patent No.: US 10,258,261 B2
(45) Date of Patent: Apr. 16, 2019

(54) SYSTEM FOR ANALYZING CUSTOMIZED TEST STRIPS

(71) Applicants: David R. Hall, Provo, UT (US); Dan Allen, Springville, UT (US); Terrece Pearman, Draper, UT (US)

(72) Inventors: David R. Hall, Provo, UT (US); Dan Allen, Springville, UT (US); Terrece Pearman, Draper, UT (US)

( * ) Notice: Subject to any disclaimer, the term of this patent is extended or adjusted under 35 U.S.C. 154(b) by 363 days.

(21) Appl. No.: 15/400,231

(22) Filed: Jan. 6, 2017

(65) Prior Publication Data

US 2018/0192925 A1 Jul. 12, 2018

(51) Int. Cl.

| | |
|---|---|
| *G01N 31/22* | (2006.01) |
| *A61B 5/145* | (2006.01) |
| *A61B 5/0205* | (2006.01) |
| *A61B 5/00* | (2006.01) |
| *A61B 7/02* | (2006.01) |
| *A61B 10/00* | (2006.01) |
| *A47K 17/02* | (2006.01) |
| *E03D 11/13* | (2006.01) |
| *G01G 19/52* | (2006.01) |
| *A61B 5/0402* | (2006.01) |
| *A61B 5/021* | (2006.01) |
| *A61B 5/053* | (2006.01) |

(Continued)

(52) U.S. Cl.
CPC ........ *A61B 5/14507* (2013.01); *A47K 17/026* (2013.01); *A61B 5/02055* (2013.01); *A61B 5/6891* (2013.01); *A61B 7/02* (2013.01); *A61B 10/007* (2013.01); *A61B 10/0038* (2013.01); *E03D 11/13* (2013.01); *G01G 19/52* (2013.01); *A61B 5/021* (2013.01); *A61B 5/0402* (2013.01); *A61B 5/053* (2013.01); *A61B 5/14532* (2013.01); *A61B 5/14551* (2013.01); *A61B 7/04* (2013.01); *A61B 8/00* (2013.01); *A61B 2560/0462* (2013.01); *A61B 2562/0295* (2013.01); *E03D 2201/00* (2013.01)

(58) Field of Classification Search
CPC ............ A61B 5/14507; A61B 5/02055; A61B 10/007; A61B 7/02; A61B 5/6891; A61B 10/0038; A61B 7/04; A61B 5/14551; A61B 8/00; A61B 2560/0462; A61B 5/14532; A61B 5/053; A61B 5/021; A61B 5/0402; A61B 2562/0295; A47K 17/026; E03D 11/13; E03D 2201/00; G01G 19/52; G01N 33/54386
See application file for complete search history.

(56) References Cited

U.S. PATENT DOCUMENTS

2008/0299005 A1* 12/2008 Meathrel ................ A61K 9/006
422/552
2016/0327553 A1* 11/2016 Edwards .............. G01N 33/493

* cited by examiner

*Primary Examiner* — Dennis White

(57) ABSTRACT

We disclose a system which may be used to analyze data collected from a customized test strip. The customized test strip may include a set of reaction pads which are selected to address the medical needs of a specific user. The system may include a data analysis platform which analyzes the data and proposes a second customized test strip. The second test strip may comprise of a set of reaction pads that the data analysis platform selects for the user based on the analysis of the first customized test strip. The data analysis platform may propose that additional diagnostic metrics be collected from the user to assist in diagnosis. The customized test strips and the additional diagnostic metrics may be within a medical toilet.

20 Claims, 8 Drawing Sheets

(51) Int. Cl.
*A61B 8/00* (2006.01)
*A61B 5/1455* (2006.01)
*A61B 7/04* (2006.01)

SYSTEM FOR ANALYZING CUSTOMIZED TEST STRIPS

BACKGROUND

Field of the Invention

This invention relates to test strips for conducting analytical assays, typically for medical use, and systems for analyzing data from test strips.

Background of the Invention

Biochemical assays using test strips for analysis of urine, blood, saliva, feces, and other biological material are often performed in a bathroom. Even when not performed in a bathroom, the test strip represents biohazard waste that must be disposed of using specific protocols. Disposal of the biowaste through the sewage system, which is suited to handle biowaste, would alleviate having to provide a separate solid waste stream.

Traditional test strips are designed to be immersed into a liquid sample or saturated by a urine stream rather than receive small volume samples through a dispenser. Consequently, they do not dissolve in the presence of aqueous solution, such as toilet water, and may not be disposed of by flushing. They typically include a layer of plastic of other hydrophobic material which will not break up in the sewer system. One purpose of the hydrophobic material is to keep the different reagents that are present on test trips from mixing when the test strip is exposed to a liquid sample. Particularly when test strips include reagents for detecting multiple analytes along the length of the test strip, the plastic keeps the test strip from absorbing the sample and drawing the different reagents along the test strip by capillary action.

Plastics or other hydrophobic material used to prevent reagent mixture on test strips are not suited for processing in the sewer system. While some plastics are biodegradable, the time scale for disintegration (for example, the INDA and EDANA standards for dispersion time) may be challenging for robust plastics. A test strip that disintegrates rapidly in water without mixing the reagents on a multi-analyte test strip is needed.

Furthermore, while some test strips may be somewhat customized for a particular type of user, they typically include reaction pads that are for a general category of user. For example, some test strips are designed with reaction pads that are generally applicable to diabetics or those with kidney or heart disease. Test strips that are designed specifically for an individual user are needed.

In addition, automation of healthcare provides faster and more efficient health services. A system which reads the result of a test strip, proposes a follow-up metric which may be a second test strip that is customized to the user and based on the results of the first test strip, and proposes diagnoses is needed.

BRIEF SUMMARY OF THE INVENTION

We disclose a novel system for analyzing customized test strips and providing information useful in assessing a user's health status. The system may analyze flushable test strips that are designed to detect a series of analytes that are relevant to the user's health. Each customized test strip may include a series of reaction pads. Each reaction pad includes a reagent that participates in a chemical reaction in the presence of a specific analyte. The chemical reaction produces a detectable product.

The system may include a detector which detects and quantifies the detectable product. The level of detectable product produced in the reaction pad may be proportional to the level of the analyte the reaction pad is designed to detect and quantify.

The system may also include a memory. The memory may store data sets from the customized test strips. The data sets may be customized test strips that were reacted with samples from the user as well as data sets from test strips that were reacted with samples from other users. Consequently, the analyte levels measured in the sample collected from the user may be compared to analyte levels from other users.

In some embodiments, the customized test strips that were reacted with samples from the user may be compared to analyte levels from other users who have been diagnosed with a specific disease. This may be particularly useful if the user is suspected of suffering from that same specific disease. Therefore, the user's pattern of analyte levels may be compared to the analyte levels of those known to have the suspected specific disease.

The system may include a data analysis platform which performs the comparisons of the data sets collected from the customized test strips with the normal ranges and with data sets stored in the memory. The data analysis platform may provide a differential diagnosis based on the analysis of the customized test strip. The data analysis platform may also propose a second customized test strips to use as follow-up metric. Furthermore, the data analysis platform may propose additional diagnostic metrics which are not test strips. The analysis of the second test strips and the results obtained from the additional diagnostic metrics may be stored in the memory. The data analysis platform may analyze these additional data. The analysis may eliminate diseases in the differential diagnosis and propose a single diagnosis.

The system may also include an output which enables a healthcare provider to view reports of data sets, proposed second customized test strips, proposed additional diagnostic metrics, differential diagnoses, and other relevant information.

DETAILED DESCRIPTION OF THE INVENTION

Definitions

Figure 1A:
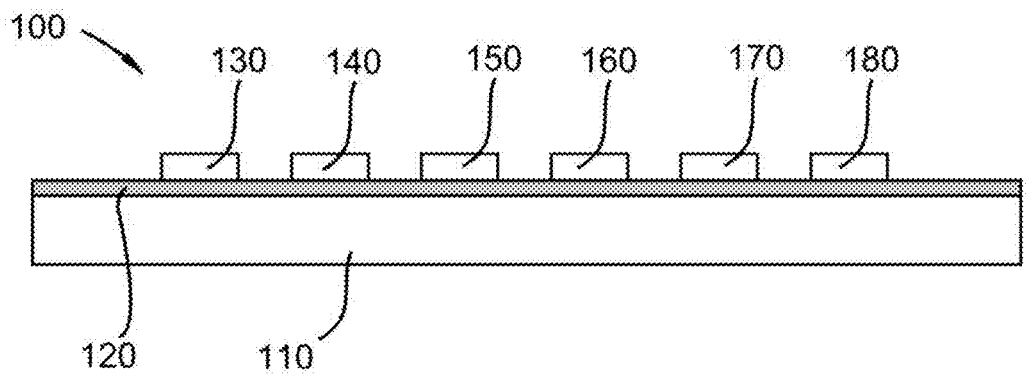
FIG. 1A is a side view of an embodiment of a test strip according to an embodiment of the invention as viewed from the long side of the test strip.

Toilet, as used herein, means a device that collects biological waste products of a mammal, including urine and feces.

Medical toilet, as used herein, means a toilet that conducts one or more measurements relevant to a user's health status. This may include, but is not limited to, quantification of analytes in urine or feces, cardiovascular parameters, bioimpedance measurements, and body weight.

User, as used herein, means any mammal, human or animal, for which the system disclosed herein is used to provide healthcare services.

Healthcare provider, as used herein, means any individual who performs a task, mental or physical, in relation to health-related services provided to a user.

Sample, as used herein, may be any biological fluid or solubilized biological material that is collected from a user. Examples include, but are not limited to, urine blood, plasma, serum, solubilized feces, vomit, gastric gavage, spinal fluid, ascites, saliva, seminal fluid, vaginal secretions, nasal mucous, breast milk, and tears.

Vertical, as used herein with regard to the disclosed customized test strip, means the plane that runs from the top to the bottom of the customized test strip when the customized test strip lays flat on a surface with the short side and long side parallel to the surface.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Disclosed herein is a novel system for analyzing customized test strips, storing and analyzing the data, and proposing follow-up diagnostic metrics. The customized test strips may be flushable test strips that are disclosed in U.S. patent application Ser. No. 15/398,052 filed on Jan. 4, 2017, which is hereby incorporated by reference in its entirety. In addition to being flushable, these customized test strips are also designed to receive a small amount of sample which may be dispensed by a precision dispenser.

The customized test strips may include a length and a width, with the length being longer than the width. This configuration allows the customized test strips to be loaded onto a dispenser so that a user may repeatedly use the same customized test strip in a convenient manner. The customized test strip may include a substrate layer which is made of a material that is either water-soluble or water-dispersible. The customized test strip may also include a hydrophobic coating that is positioned between the substrate layer and a layer that includes multiple reaction pads, each of which may include a liquid absorbent material. The reaction pads may each include a reagent that may participate in a chemical reaction in the presence of a specific analyte. The combination of reaction pads may be customized for a user.

For example, the user may have a medical history of heart and kidney disease. The customized test strip may include a selection of reaction pads that include markers for heart disease and markers for kidney disease. The customized test strip may also include reaction pads that test for physiological conditions that tend to be associated with false positive or false negative results when measuring the analytes that are detected by the other reaction pads on the test strip.

The reaction pads on the customized test strips may include one or more vertical cross-sections that have at least two sides that are slanted relative to the vertical axis. In some embodiments, the cross-section may be trapezoidal in shape with the wider side of the trapezoid nearest the substrate layer and the shorter side of the trapezoid on the top of the customized test strip nearest the reaction pads. In other embodiments, the cross-section of the may approximate a parallelogram. In some embodiments, the beveled cuts may be parallel to the long side of the customized test strip while in other embodiment, the beveled cuts may be parallel to the short side of the customized test strip. When the sample is loaded onto the beveled cut edges, liquid is absorbed into the reaction pad more readily than when dropped on top of the reaction pad where the material has not been cut. This is because the material often includes a coating that is water repellant causing the liquid to bead up on its surface.

The system may also include a detector which may analyze the products of the chemical reactions in the reaction pads. The detector may perform spectral analysis including, but not limited to, colorimetric or fluorescent measurements. The detector also measure changes in temperature or emission of volatile compounds that may occur in response to the reaction.

The system may also include a memory which may be within a computer. The memory may store the data sets that are created when the detector analyzes a customized test strip. The memory may store multiple data sets collected from multiple customized test strips from the same user. It may also store data sets from customized test strips which were reacted with samples from multiple users. Furthermore, the memory may store normal ranges for the analytes detected by the reaction pads and data sets collected from medical devices other than the customized test strips.

The system may include a data analysis platform which may include a machine readable medium. The data analysis platform may be programmed to compare the analysis of the reaction pads that the detector collected with normal ranges for the analytes. The normal ranges may be stored in the memory. The data analysis platform may also compare the user's data set collected from a customized test strip with other data sets stored in the memory. These other data sets may be results collected from customized test strips which were reacted with samples from other users. This provides a comparison with a analyte levels from other users who may be healthy or have been diagnosed with a disease from which the user is suspected to suffer from. For example, the user's data set from the customized test strip may be compared to patterns of analyte levels detected in users who have been diagnosed with a particular type of heart disease. It may be informative to know if the user's analyte levels match those of known heart disease patients.

Alternatively, the user may collect a data set from a customized test strip over time at defined time intervals. Each time, the new data set may be stored in the memory. Eventually, enough data sets may be collected to perform a trending analysis of the user's analyte levels over time.

The system may also include an output which may be include physical electrical interconnects from the memory. The output may include a computer screen which may communicate data sets, calculations, and other information to a user or healthcare provider.

In some embodiments, the data analysis platform may analyze the customized test strip and identify a series of follow-up analyte assays to perform on a sample from the user. These follow-up analyte assays may provide more conclusive information which may be used by a healthcare provider to provide a diagnosis. These follow-up analyte assays may be a series of reaction pads on a second customized test strip which may be selected based on the results collected from the first customized test strip. The second customized test strip may include the same dimensions and materials as the first customized test strip except for the different reagents in the reaction pads. For example, the second test strip may have approximately the same length and width as the first customized test strip. It may include a substrate layer, a hydrophobic coating, and multiple reaction pads, each including a liquid absorbent material and a reagent which participates in a chemical reaction in the presence of a specific analyte. As with the first customized test strip, the hydrophobic coating may be between the substrate layer and the reaction pads. Furthermore, the second customized test strip may be cut so that a vertical cross-section of reach of the reaction pads has at least two sides which are slanted relative to the vertical axis.

The output may propose the second customized test strip when reporting the analysis of the first customized test strip. Should the second customized test strip be reacted with a sample from the user, the detector may analyze the reaction products on the reaction pads of the second customized test strip. The data analysis platform may then compare the analysis with a normal range of the analytes that may be stored in the memory. As with the first customized test strip, the analysis of the second customized test strip may be compared to other data sets collected either from the user or from other users, each of which may be stored in the memory. The other users may be individuals who have been diagnosed with the same disease that the user is suspected of having based on the results of the first customized test strip. Consequently, the pattern of analyte levels identified in the user may be compared to analyte levels from individuals known to suffer from a particular disease.

The data analysis platform may identify a differential diagnosis based at least on the results of the first customized test trip or based on both the first customized test strip and the second customized test strip. The output may report the differential diagnosis. The output may propose additional customized test strips to distinguish between the components of the differential diagnosis. Alternatively, the system may propose an additional diagnostic metric which is not a test strip as a follow-up diagnostic metric. These additional diagnostic metrics may include ultrasound imaging, electrocardiogram readings, biopsies, and other medical diagnostic methods known in the art. The result from the additional diagnostic metric may be stored in the memory. The data analysis platform may use the data from the additional diagnostic metric to select a single diagnosis from the differential diagnosis. The output may report the single diagnosis.

In some embodiments, the disclosed system may include a medical toilet. The medical toilet may include a collection system for collecting samples from a user. The collection system may include or be connected to a precision dispenser which loads a small volume of sample onto a customized test strip. The medical toilet may include the memory. In some embodiments, the memory may be located outside the medical toilet and the data set transmitted through a data port from the medical toilet to the memory.

The medical toilet may also include medical devices for collecting additional diagnostic metrics other than test strips. In the event that the data analysis platform identifies a need for an additional diagnostic metric based on the results of a customized test strip, the additional diagnostic metric may also be collected by the medical toilet, stored in the memory, and analyzed by the data analysis platform.

Referring now to the drawings, FIG. 1A illustrates customized test strip 100, which is an embodiment of a customized test strip which may be used in the disclosed system. Customized test strip 100 includes substrate layer 110 and reaction pads 130, 140, 150, 160, 170, and 180. Hydrophobic coating 120 is between substrate layer 110 and reaction pads 130, 140, 150, 160, 170, and 180. In customized test strip 100, each of the reaction pads 130, 140, 150, 160, 170, and 180 includes a different reagent that reacts in the presence of a different analyte. The reaction pads may be created by laying multiple strips of reagent paper, each including a different reagent, on a panel of substrate. The panel may then be sliced across each of the reagent strips to create multiple customized test strips, each with a section of the multiple reagent papers.

Figure 1B:
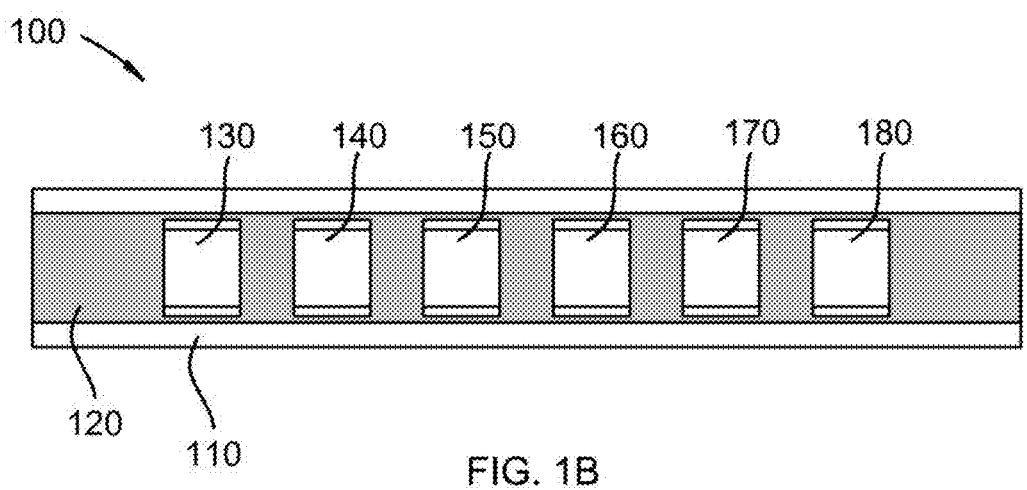
FIG. 1B is an aerial view of the test strip of FIG. 1A.

FIG. 1B is an aerial view of customized test strip 100. Reaction pads 130, 140, 150, 160, 170, and 180 are visible as well as parts of hydrophobic coating 120 which runs continuously beneath and between reaction pads 130, 140, 150, 160, 170, and 180 and above substrate layer 110.

Figure 1C:
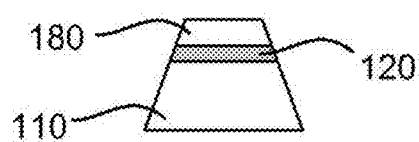
FIG. 1C is a side view of the test strip of FIGS. 1A and 1B from the short side of the test strip.

FIG. 1C is a side view of customized test strip 100 which is a 90-degree rotation of test strip 100 as shown in FIG. 1A. Reagent pad 180 is shown above hydrophobic coating 120 and substrate layer 110. The beveled sides of test strip 100 are shown in this view which create a trapezoidal cross section. The sides of reaction pads 130, 140, 150, 160, 170, and 180 along the long side are angled toward the center of customized test strip 100 (away from the plane of the paper in the drawing). In some embodiments, the long side of customized test strip 100 may be moved along a dispenser and the bevel-cut sides may absorb liquid as test strip 100 moves along. Liquid sample is more readily absorbed through the sides due to the angle of the cut, the trapezoidal shape, and the exposed cut paper fibers.

Figure 2:
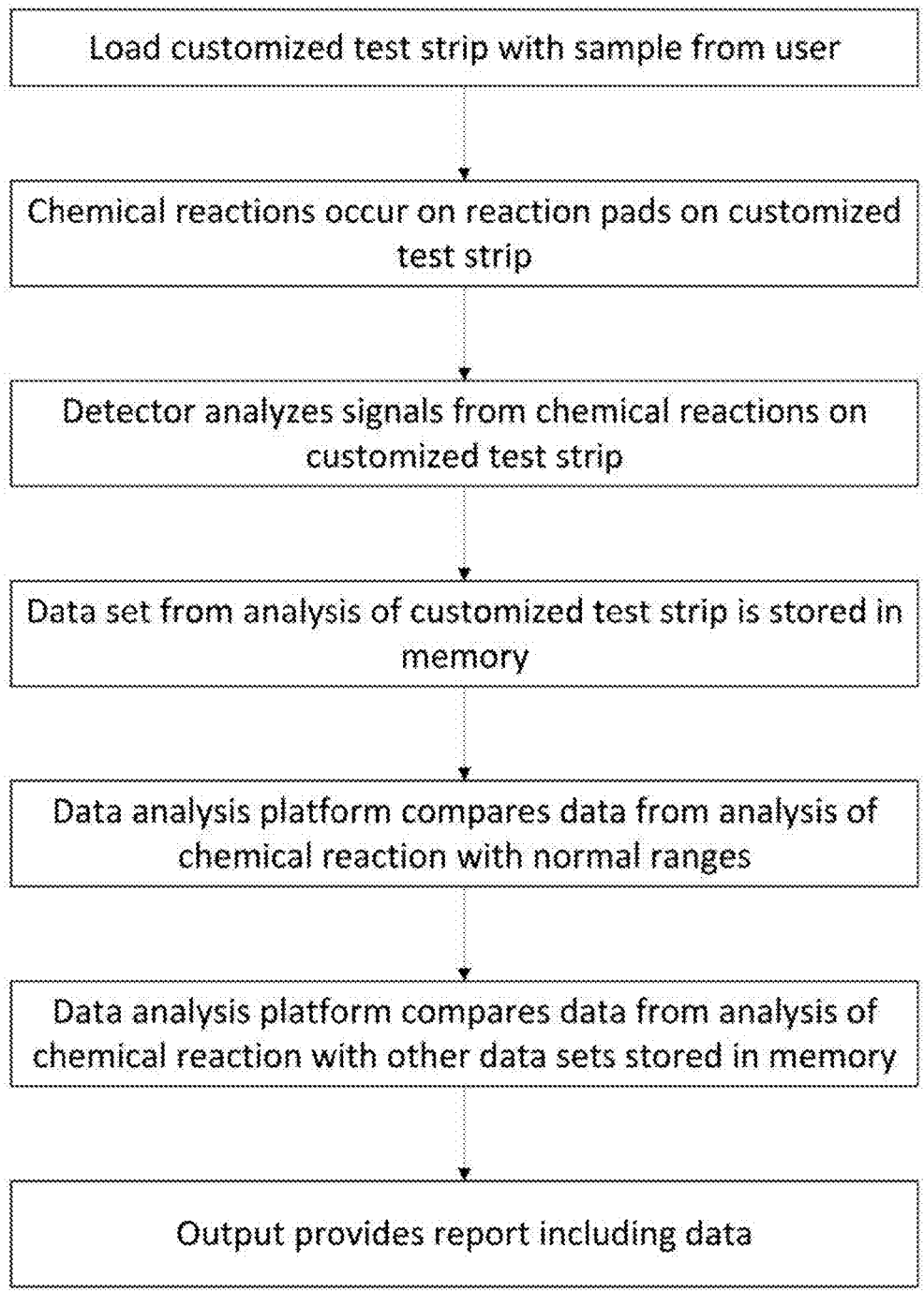
FIG. 2 is a flow chart illustrating steps that may be followed during use of the disclosed system.

FIG. 2 is a flow chart illustrating a series of steps which may be performed during use of an embodiment of the disclosed system. A sample collected from a user may be loaded onto a customized test strip. Loading may be performed using a precision dispenser which applies a small volume of sample to the cut edge of the reaction pads on the customized test strip. The chemical reactions occur on the reaction pads of the customized test strips which create detectable reaction producst in the presence of specific analytes that may be present in the user's sample. The detector then analyzes the signals from the reaction products. These signals may be colorimetric, fluorescent, thermal, or other products of chemical reactions known in the art. The data set collected by the detector may then be stored in the memory. The data analysis platform may then perform comparisons of the data set collected from the customized test strip with a range of normal analyte levels that may be stored in the memory. The data analysis platform may also compare the data set collected from the customized test strip with other data sets stored in the memory. The output then may provide a report that may include the data set from the customized test strip, how the analyte levels compare to normal ranges, and comparisons to other data sets that may have been performed. A healthcare provider may use this report to assess the user's health status.

Figure 3:
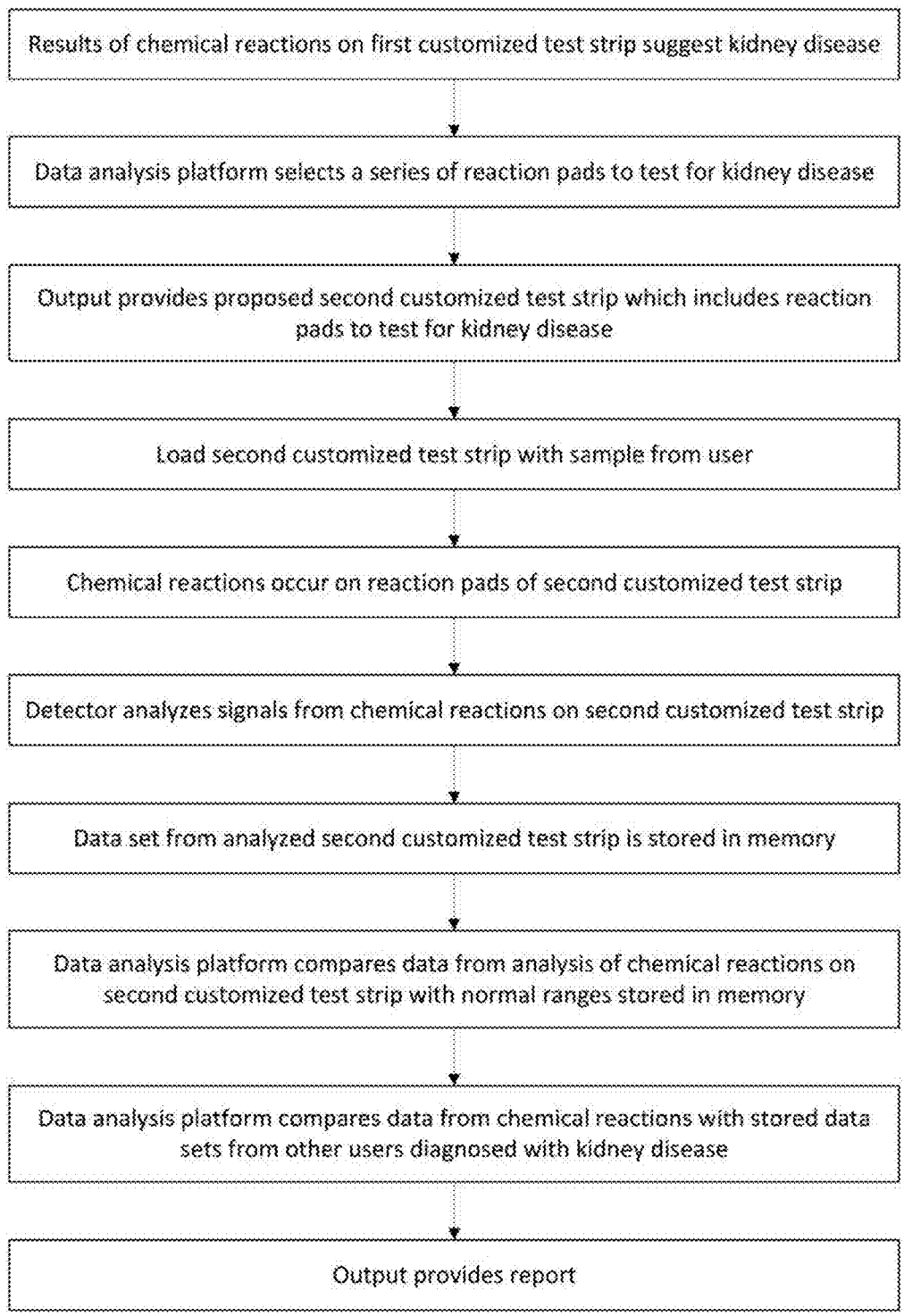
FIG. 3 is a flow chart illustrating steps that may be followed during use of the disclosed system in which a second customized test strip is used.

FIG. 3 is a flow chart which illustrates series of steps which may be performed during use of an embodiment of the disclosed system in which a second customized test strip is used to analyze the components of a sample collected from a user. In this example, the results from the chemical reactions on a first customized test strip have been analyzed. The report provided by the output suggests that the user may suffer from kidney disease. The data analysis platform then selects a series of reaction pads which detect analyte levels which may be used to further address the possibility that the user suffers from kidney disease, and perhaps, assess what type of kidney disease may be present. The second customized test strip is obtained and a sample from the user is loaded onto the second customized test strip. Chemical reactions occur on the second customized test strip in the presence of specific analytes and the detector analyzes the signals. The data set from the second customized test strip is stored in the memory and the data analysis platform compares the data set with normal ranges of the analytes stored in the memory. The data analysis platform then compares the data set from the test strip with data sets stored in the memory that were collected from other users who have been diagnosed with kidney disease. The data set and the comparisons are then provided in a report that is visible through the output. Even if it is not known why the analytes are outside the normal range in users that suffer from kidney disease, the comparison of the user's data with the pattern of analyte levels with those that are known to have kidney disease may be helpful in providing a diagnosis for the user. As one of skill in the art will understand, the example of kidney disease is merely illustrative and other disease processes may similarly be assessed with the disclosed system.

Figure 4:
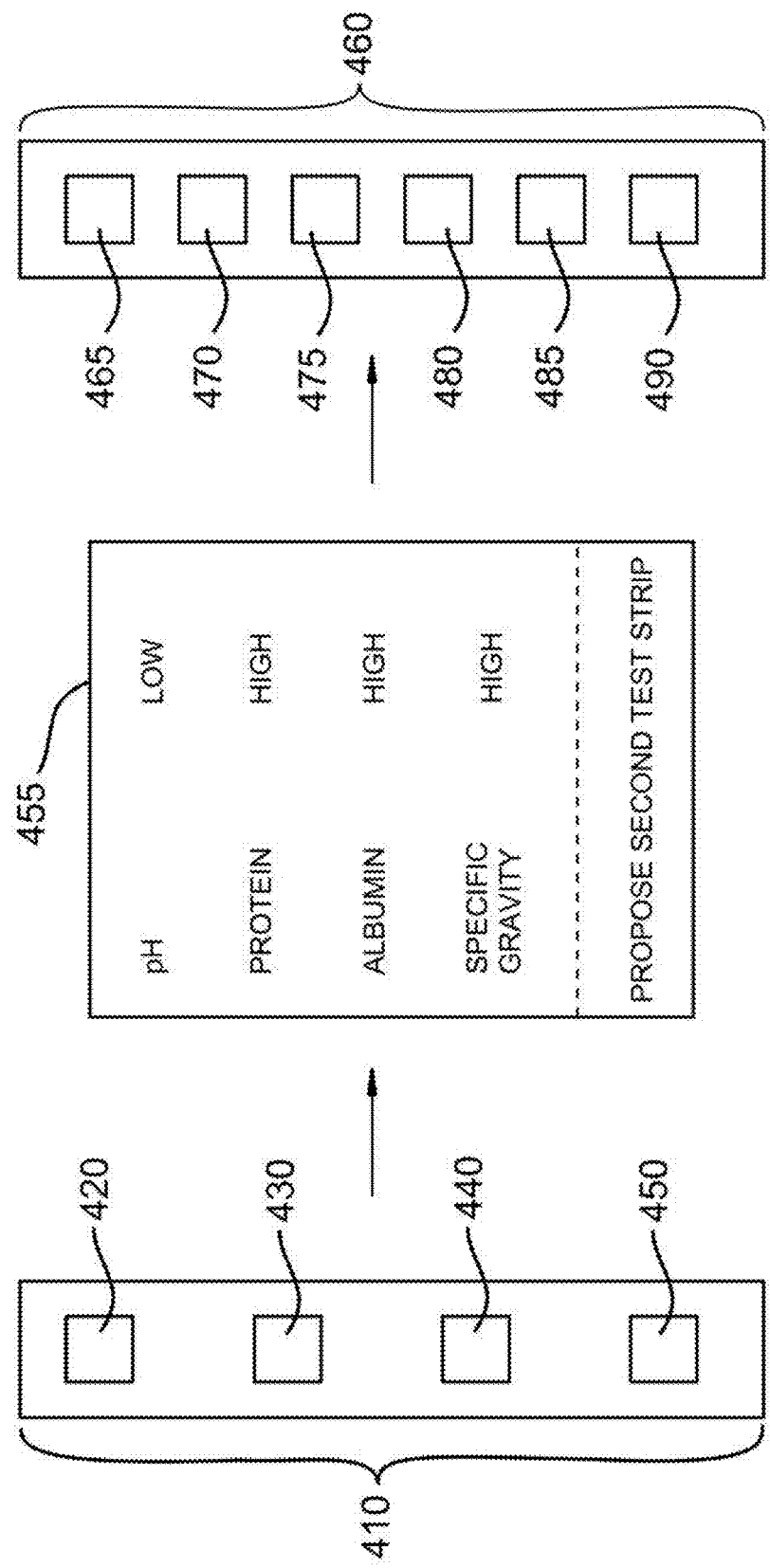
FIG. 4 is an illustration of a first customized test strip, the results provided by the first customized test strip as seen on an output device, and a proposed second customized test strip.

FIG. 4 further illustrates an example in which a first customized test strip and a second customized test strip are to diagnose kidney disease in a user. First test strip 410 includes reaction pads 420, 430, 440, and 450. The reaction pads in the example of FIG. 4 detect and quantify the following analytes in urine: pH (reaction pad 420), protein (reaction pad 430), albumin (reaction pad 440), and specific gravity (reaction pad 450). The series of steps described in the flow chart of FIG. 3 are performed and output 455 reports the comparison of the analyte levels in the user's urine sample with a range of normal levels that is stored in the memory. In this example, the output reports that the pH is low, and protein, albumin, and specific gravity are high relative to normal ranges. This data set suggests that the user may suffer from improperly functioning kidneys.

The data analysis platform has also designed a second customized test strip which includes reaction pads to provide further information about the user's kidney function. Output 455 proposes the use of second customized test strip 460. Second customized test strip 460 includes reaction pads 465, 470, 475, 480, 485, and 490. The reaction pads on second customized test strip 460 detect and quantify additional analytes that are relevant to kidney disease. These include creatinine, nitrates, blood, ketones, glucose, and leukocyte esterase. The analysis of second customized test strip 460 may then be used to further assess the user's kidney function.

Figure 5:
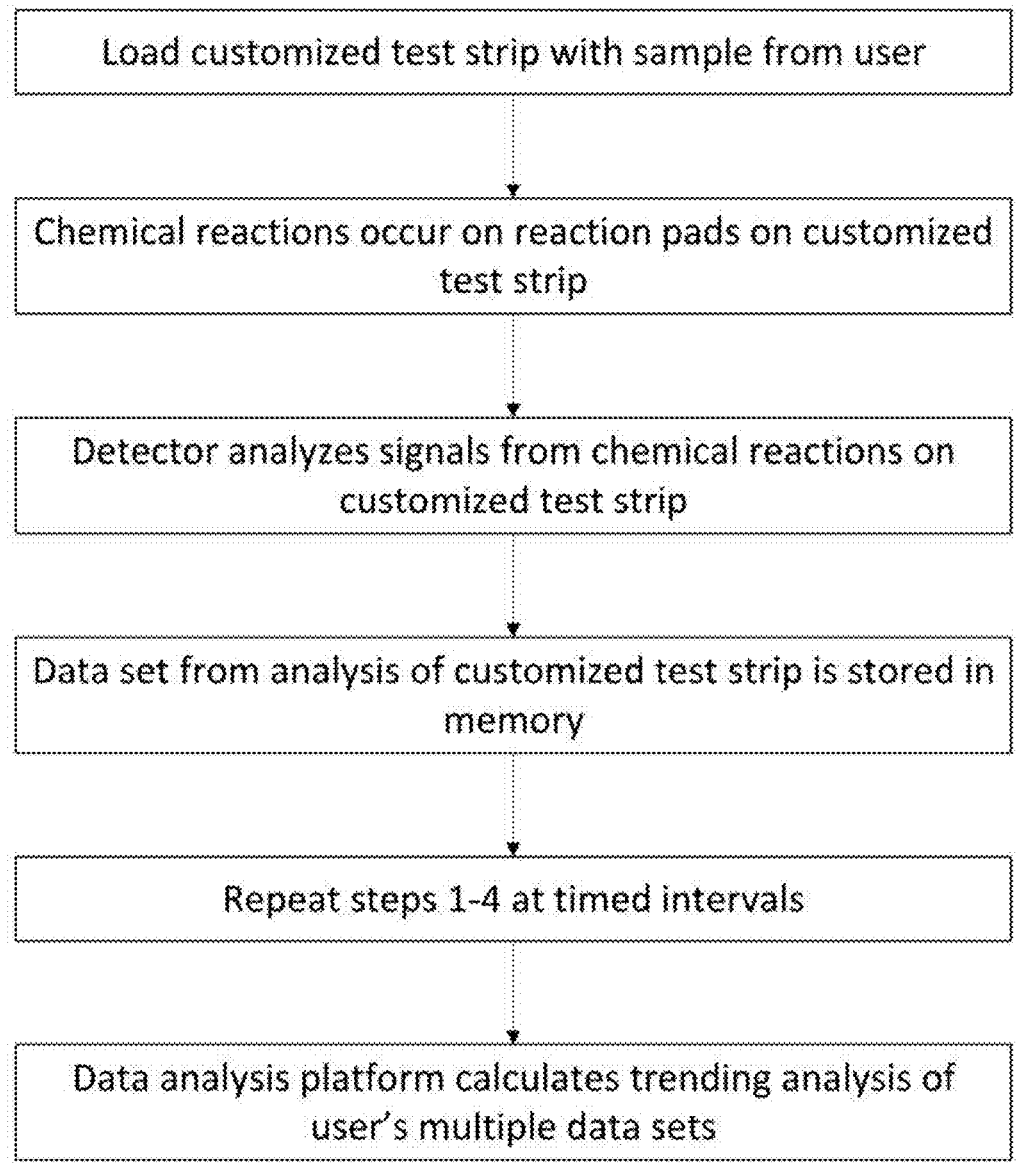
FIG. 5 is a flow chart illustrating steps that may be followed during use of the disclosed system in which a trending analysis is performed using multiple data sets collected from the same user.

FIG. 5 is a flow chart illustrating a series of steps which may be used in an embodiment of the disclosed system. This series of steps may be used to create a trending analysis of the user's analyte levels over time. In this embodiment, a sample collected from a user is loaded onto a customized test strip. Chemical reactions then occur on the reaction pads on the customized test strip producing detectable products in the presence of specific analytes. The detector quantifies the detectable products by measuring signals they produce. The data set from the analysis of the reaction pads is stored in the memory. This series of steps is repeated at timed intervals using a fresh customized test strip that includes the same reaction pads. Consequently, the same analytes are monitored over time. The data analysis platform then calculates a trending analysis using the multiple data sets collected from the user.

Figure 6:
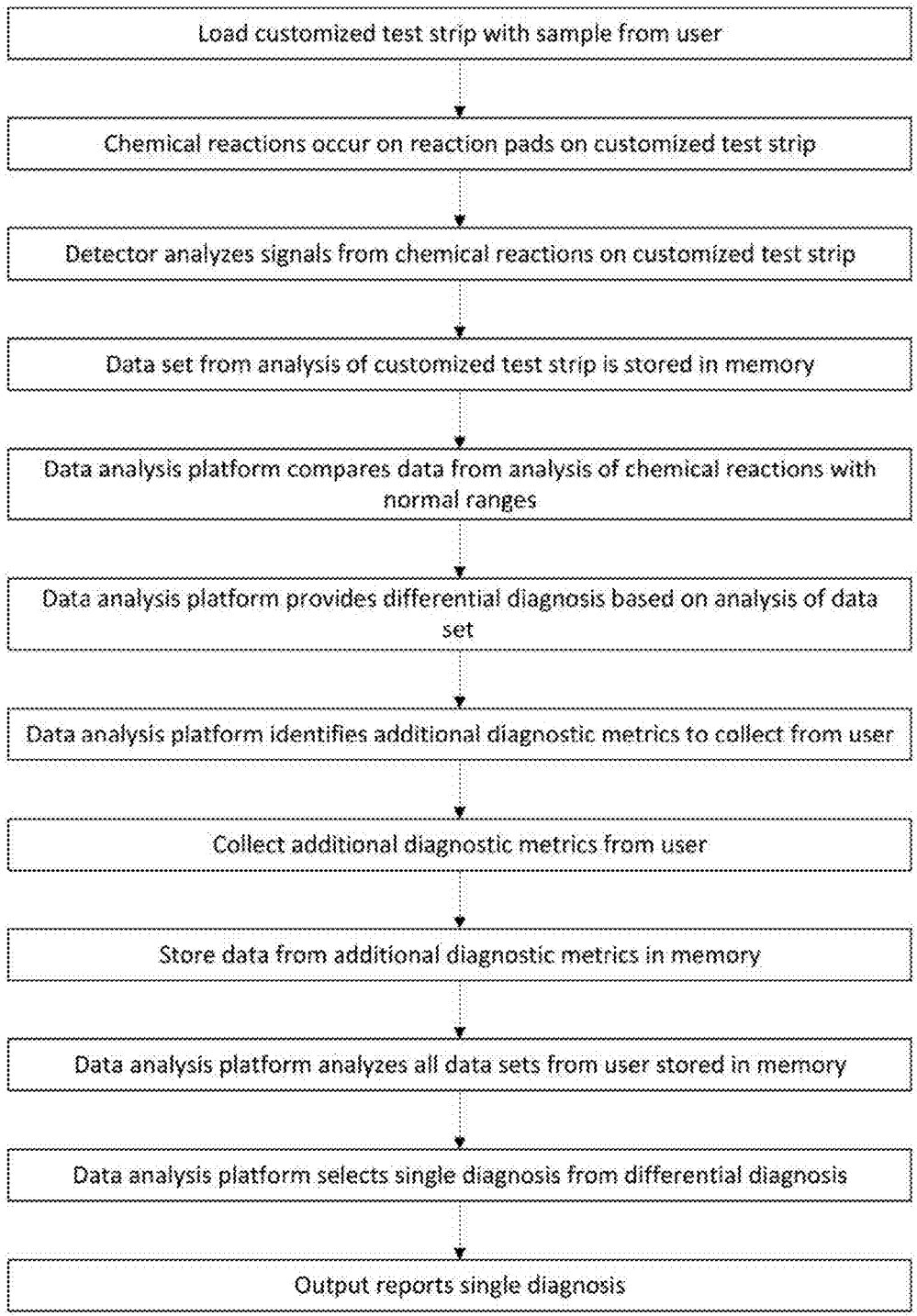
FIG. 6 is a flow chart illustrating steps that may be followed during use of the disclosed system in which the system provides a differential diagnosis.

FIG. 6 is a flow chart illustrating a series of steps which may be used in an embodiment of the disclosed system. This series of steps may be used to obtain a differential diagnosis and then a single diagnosis of a user's disease.

In the embodiment of FIG. 6, a sample is collected from a user and loaded onto a customized test strip. Chemical reactions occur within the reaction pads on the customized test strips in the presence of specific analytes that may be present in the sample. Detectable reaction products are produced which emit a detectable signal. The detector analyses the signals from the products of the chemical reactions in the reaction pads and the data set is stored in the memory. The data analysis platform analyzes the data set and compares the results to normal ranges for the analytes that may be stored in the memory.

In the event that any of the analyte levels fall outside the normal range for that analyte, the data analysis platform may provide a differential diagnosis for the user based on the data set. The data analysis platform may propose an additional diagnostic metric be collected from the user which may provide additional information related to the user's health status and distinguish between the diseases in the differential diagnosis. The additional diagnostic metric may be a technique other than a test strip. For example, the data analysis platform may determine that an electrocardiogram reading and an echocardiogram are needed to diagnose or exclude specific types of heart disease that are present in the differential diagnosis. The additional diagnostic metrics may be stored in the memory along with the data sets from the customized test strips. The data analysis platform may use the combined data for the user that is present in the memory to select a single diagnosis for the user. The output may then report the single diagnosis. A healthcare provider may then proceed with treatment.

Figure 7:
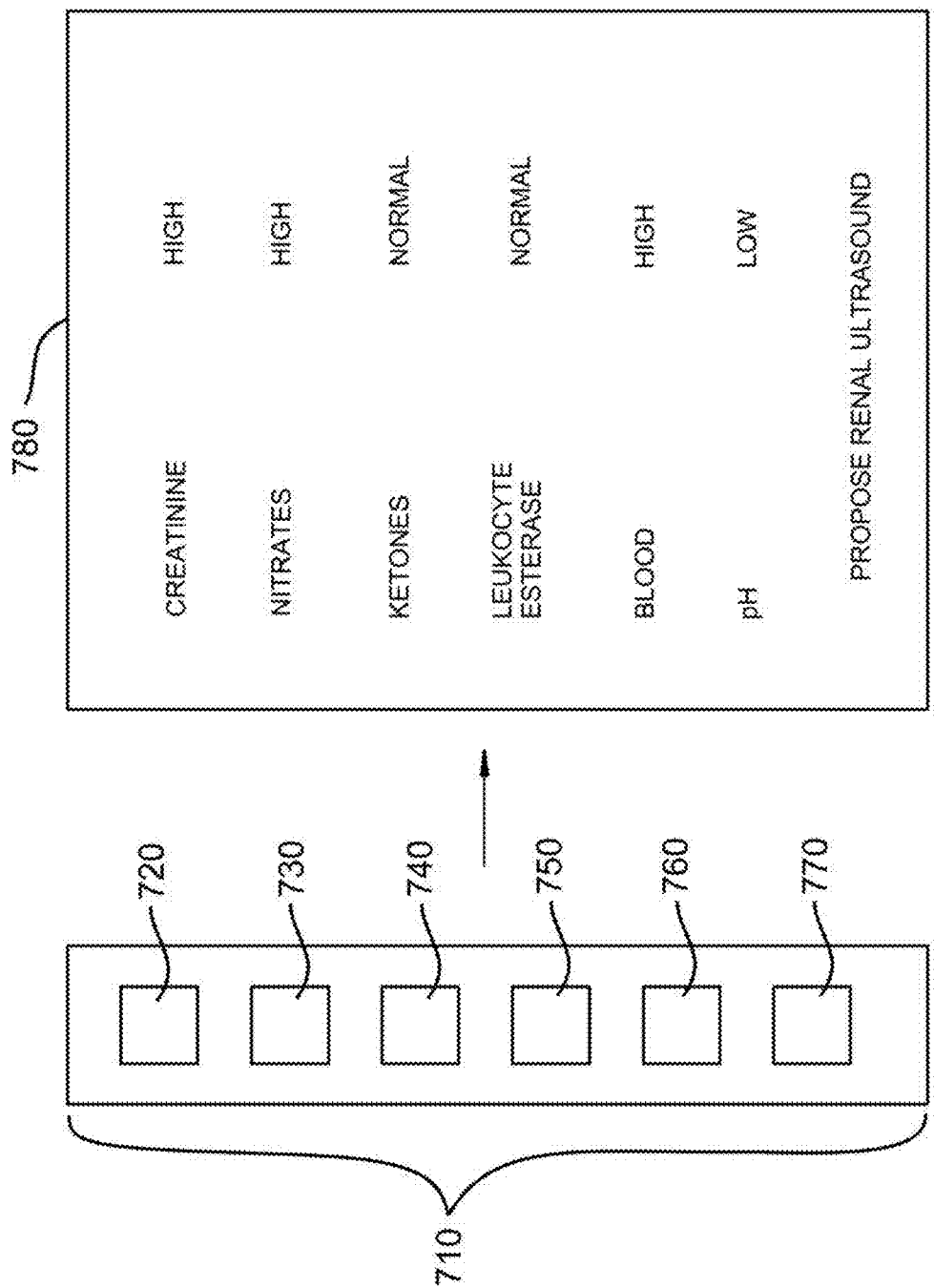
FIG. 7 is an illustration of a customized test strip and a report which provides the results from the test strip and proposes an additional diagnostic metric.

FIG. 7 illustrates an embodiment of the use of the steps of FIG. 6 in which the data analysis platform proposes the use of an additional diagnostic metric. Customized test strip 710 includes reaction pads 720, 730, 740, 750, 760, and 770. In this example, the reaction pads detect creatinine, nitrates, leukocyte esterase, blood, and pH respectively in a urine sample.

Output 780 provides a report of the data set collected by customized test strip 710. Output 780 reports that urine creatinine is high and there is blood present in the user's urine. Levels of ketones and leukocyte esterase are normal but the user's urine pH is abnormally low. The data analysis platform has proposed that an ultrasound analysis of the user's kidney would provide useful diagnostic information. This proposal is provided in a report shown in output 780.

Figure 8:
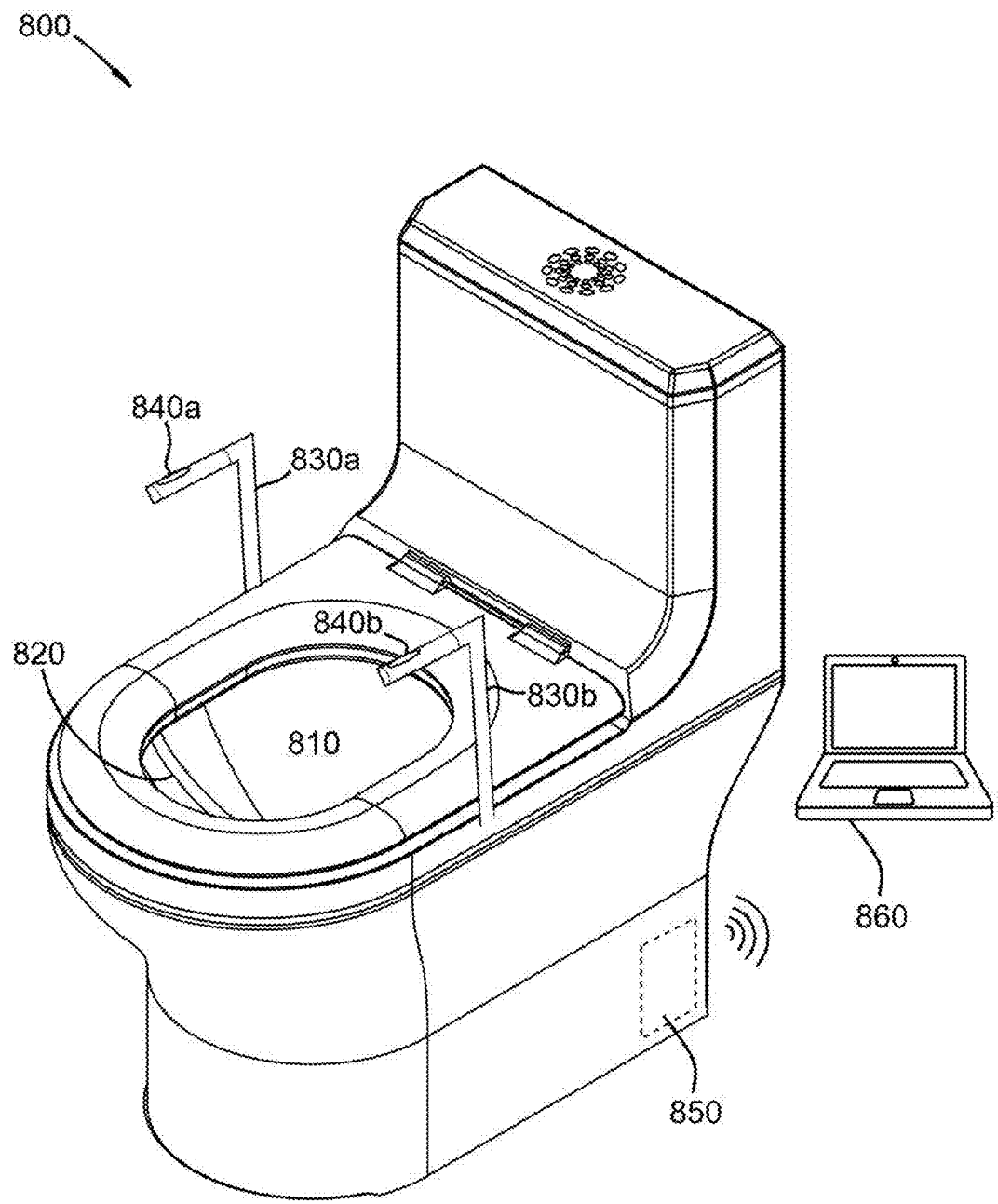
FIG. 8 is an illustration of a medical toilet which may include customized test strips and an additional diagnostic metric.

In some embodiments, the customized test strips, the medical devices which collect additional diagnostic metrics, or both are within a medical toilet. FIG. 8 illustrates medical toilet 800 which is an embodiment of a medical toilet which may be used to collect data sets from customized test strips and additional diagnostic metrics. Medical toilet 800 includes toilet bowl 810. Urine collection system 820 is shown within toilet bowl 810. A user may urinate normally into medical toilet 800 and urine collection system 820 may collect a small sample of the user's urine. Urine collection system 820 includes a precision dispenser which loads a small volume of urine onto a customized test strip within medical toilet 800. Handles 830a and 830b are included on medical toilet 800. Handles 830a and 830b includes sensors 840a and 840b respectively. Sensors 840a and 840b detect a user's heart rate when the user grasps each of handles 830a and 830b with a hand. The heart rate may be an additional diagnostic metric proposed in the embodiment of FIG. 6. Medical toilet 800 further includes memory 850 which may store data collected by medical toilet 800. In other embodiments, memory 850 may be located outside of medical toilet 800 and receive data from the detector through a data port.

In the embodiment of FIG. 8, computer 860 includes the data analysis platform which receives data from medical toilet 800 through wireless transmission. The output of the system may be displayed on the screen of computer 860.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A system for assessing the health of a user, the system comprising:
    a first customized test strip comprising:
        a length and a width, wherein the length is greater than the width;
        a substrate layer, wherein the substrate layer comprises a material that is water-soluble or water-dispersible, and a first side;
        a first hydrophobic coating; and
        a first plurality of reaction pads, wherein each of the first plurality of reaction pads comprises a reagent that participates in one of a first plurality of chemical reactions in the presence of one of a first plurality of analytes, wherein each of the first plurality of chemical reactions forms a detectable product, wherein the first hydrophobic coating is between the first side of the substrate layer and the first plurality of reaction pads, and wherein the first plurality of reaction pads is customized for a user; and
        wherein at least one vertical cross-section of each of the first plurality of reaction pads comprises at least two sides that are slanted relative to a vertical axis;
    a detector which performs analysis of the detectable product on each of the first plurality of reaction pads;
    a memory for storing a plurality of data sets;
    a data analysis platform, wherein the data analysis platform performs a comparison of the analysis of the detectable product on each of the first plurality or reaction pads with a normal range for each of the first plurality of analytes stored in the memory;
    an output formed of one or more physical electrical interconnects from the memory for communicating data.

2. The system of claim 1, wherein the data analysis platform further performs a comparison of the analysis of the detectable product on each of the first plurality of reaction pads with at least one data set stored in the memory.

3. The system of claim 2, wherein the at least one data set stored in the memory is collected from the user.

4. The system of claim 1, wherein the at least one data set stored in the memory is collected from at least one other user.

5. The system of claim 1, wherein the at least one vertical cross-section of each of the first plurality of reaction pads comprises a first vertical cross-section which is parallel to the width of the first customized test strip and is approximately trapezoidal in shape.

6. The system of claim 5, wherein at least one vertical cross-section of each of the first plurality of reaction pads further comprises a second vertical cross-section which is parallel to the length of the first customized test strip and is approximately trapezoidal in shape.

7. The system of claim 1, wherein the data analysis platform further proposes a second customized test strip for the user, wherein the second customized test strip comprises:
    the length and the width of the first customized test strip;
    the substrate layer of the first customized test strip;
    the first hydrophobic coating of the first customized test strip; and
    a second plurality of reaction pads wherein each of the second plurality of reaction pads comprises a reagent that participates in one of a second plurality of chemical reactions in the presence of an analyte, wherein each of the second plurality of chemical reactions forms a detectable product, wherein the first hydrophobic coating is between the first side of the substrate layer and the second plurality of reaction pads; and
    wherein at least one vertical cross-section of each of the second plurality of reaction pads comprises at least two sides that are slanted relative to a vertical axis,
    wherein the data analysis platform performs a comparison of the analysis of the detectable product on each of the second plurality or reaction pads with a normal range for each of the second plurality of analytes stored in the memory, and
    wherein data analysis platform selects the second plurality of reaction pads based on the comparison of the analysis of the detectable product on each of the first plurality or reaction pads with the normal range for each of the first plurality of analytes stored in the memory.

8. The system of claim 7, wherein data analysis platform further performs a comparison of the analysis of the detectable product on each of the second plurality of reaction pads with at least one data set stored in the memory.

9. The system of claim 8, wherein the at least one data set was collected from the user.

10. The system of claim 8, wherein the at least one data set was collected from at least one other user.

11. The system of claim 10, wherein the at least one other user has been diagnosed with a same or similar disease.

12. The system of claim 7, wherein the at least one vertical cross-section of each of the second plurality of reaction pads comprises a first vertical cross-section which is parallel to the width of the second customized test strip and is approximately trapezoidal in shape.

13. The system of claim 12, wherein at least one vertical cross-section of each of the second plurality of reaction pads further comprises a second vertical cross-section which is parallel to the length of the second customized test strip and is approximately trapezoidal in shape.

14. The system of claim 7, wherein the at least one vertical cross-section of each of second plurality of reaction pads comprises a first vertical cross-section which is parallel to the length of the second customized test strip and is approximately a parallelogram.

15. The system of claim 7, wherein the data analysis platform further prepares a first differential diagnosis, wherein the first differential diagnosis comprises one or more diseases that are consistent with the analysis of the detectable product on each of the first plurality or reaction pads and the analysis of the detectable product on each of the second plurality or reaction pads.

16. The system of claim 15, wherein the data analysis platform further proposes one or more additional diagnostic metrics to be collected from the user, wherein the one or more additional diagnostic metrics test for at least one of the one or more diseases.

17. The system of claim 16, wherein the memory stores one or more results of the one or more additional diagnostic metrics, and wherein the data analysis platform prepares a second differential diagnosis based on an analysis of the following data sets:

the one or more results of the one or more additional diagnostic metrics;

the comparison of the analysis of the detectable product on each of the first plurality of reaction pads with the normal range for each of the first plurality of analytes stored in the memory; and the comparison of analysis of the detectable product on each of the second plurality of reaction pads with the normal range for each of the second plurality of analytes stored in the memory.

18. The system of claim 17, wherein the additional diagnostic metrics are performed by a medical toilet.

19. The system of claim 18, wherein the medical toilet comprises one or more of the following medical devices:

a glucometer, a blood sample analyzer, an otoscope, a stethoscope, a blood pressure monitor, a body temperature sensor, a pulse oximeter, an ophthalmoscope, and an electrocardiogram unit, an ultrasound device, a body weight sensor, a bioimpedance measurements sensor, and a tissue imager.

20. The system of claim 18, wherein each of the first customized test strip and the second customized test strip are both loaded with a sample and analyzed within the medical toilet.

* * * * *